(12) United States Patent
Maris

(10) Patent No.: US 8,537,363 B2
(45) Date of Patent: Sep. 17, 2013

(54) PICOSECOND ULTRASONIC SYSTEM INCORPORATING AN OPTICAL CAVITY

(75) Inventor: Humphrey J. Maris, Barrington, RI (US)

(73) Assignee: Brown University, Providence, RI (US)

( * ) Notice: Subject to any disclaimer, the term of this patent is extended or adjusted under 35 U.S.C. 154(b) by 803 days.

(21) Appl. No.: 12/312,692

(22) PCT Filed: Nov. 19, 2007

(86) PCT No.: PCT/US2007/024125
§ 371 (c)(1),
(2), (4) Date: Feb. 26, 2010

(87) PCT Pub. No.: WO2008/069916
PCT Pub. Date: Jun. 12, 2008

(65) Prior Publication Data
US 2010/0157316 A1    Jun. 24, 2010

Related U.S. Application Data

(60) Provisional application No. 60/860,261, filed on Nov. 21, 2006.

(51) Int. Cl.
*G01B 11/06* (2006.01)
*G01N 21/55* (2006.01)
(52) U.S. Cl.
USPC .......................................... 356/445; 356/630
(58) Field of Classification Search
USPC ............................................... 356/432, 445
See application file for complete search history.

(56) References Cited

U.S. PATENT DOCUMENTS

| 5,748,317 | A | 5/1998 | Maris et al. | 356/357 |
|---|---|---|---|---|
| 5,748,318 | A | 5/1998 | Maris et al. | 346/381 |
| 5,844,684 | A | 12/1998 | Maris et al. | 356/432 |
| 5,864,393 | A | 1/1999 | Maris | 356/28 |
| 5,959,735 | A | 9/1999 | Maris et al. | 356/381 |
| 6,025,918 | A | 2/2000 | Maris | 356/388 |
| 6,038,026 | A | 3/2000 | Maris | 356/357 |
| 6,317,216 | B1 | 11/2001 | Maris | 356/496 |
| 6,321,601 | B1 | 11/2001 | Maris | 73/657 |
| 6,512,586 | B2 * | 1/2003 | Maris | 356/432 |
| 2004/0063214 | A1 | 4/2004 | Berlin et al. | 436/94 |
| 2006/0027021 | A1 | 2/2006 | Choi et al. | 73/579 |

OTHER PUBLICATIONS

Bartels et al., "Femtosecond Time-Resolved Optical Pump-Probe Spectroscopy at kHzscan-rates over ns-time-delays without mechanical delay line", Appl. Phys. Lett 88, 041117 (2006), (3 pages).

* cited by examiner

*Primary Examiner* — Gregory J Toatley
*Assistant Examiner* — Rebecca C Bryant
(74) *Attorney, Agent, or Firm* — Merchant & Gould PC

(57) ABSTRACT

A method for characterizing a sample is described. The method includes applying a first pulse of electromagnetic radiation to the surface of the sample and thus creating a propagating strain pulse within the sample. A second pulse of second electromagnetic radiation is applied to the surface of the sample so as to intercept the propagating strain pulse. The first and second pulses are applied through a structure, such as a reflector, that is disposed over the surface of the sample at a distance predetermined to form an optical cavity; the cavity having a width related to a wavelength of the second electromagnetic radiation. The method includes detecting at least one optical property of a reflection of the second pulse from the sample. The detected optical property(ies) of the reflection are associated with a characteristic of the sample. An apparatus, computer-readable medium and structure are also described.

25 Claims, 6 Drawing Sheets

PICOSECOND ULTRASONIC SYSTEM INCORPORATING AN OPTICAL CAVITY

CROSS REFERENCE TO RELATED APPLICATIONS

This application claims benefit to PCT/US2007/0241254 filed Nov. 19, 2007, which claims benefit to U.S. Provisional Application Ser. No. 60/860,261 filed Nov. 21, 2006, the disclosures of which are hereby incorporated by reference in their entirety.

FIELD OF THE INVENTION

The invention concerns an apparatus and method for making ultrasonic measurements to determine the properties of thin films, or other small structures, or to study the properties of the surface of a material.

BACKGROUND OF THE INVENTION

In the picosecond ultrasonics technique, a short light pulse (the "pump") is directed at the surface of the sample that is to be studied. When the light is absorbed, the temperature of the material near to the surface is raised slightly and a thermal stress is set up. This stress launches a strain pulse into the sample. The strain pulse is partially reflected at each interface that it encounters, thereby giving rise to reflected pulses that propagate back towards the sample surface. When one of these returning strain pulses reaches the sample surface, it causes a change in the optical reflectivity of the structure. This change is measured by means of a time-delayed light pulse (the "probe"). This technique makes it possible to perform ultrasonic experiments on a wide range of thin films and nanostructures. It is possible to measure the properties of a stack of thin films on a substrate and also to study films that have been laterally patterned.

The picosecond ultrasonics technique can be used to provide a non-destructive measurement of the thickness of thin films, particularly metal or other opaque films. The time, $\tau$, for the sound pulse to make a round trip through a film is measured. This time equals $2d/v_1$, where d is the film thickness and $v_1$ is the longitudinal sound velocity.

For most materials the sound velocity is well known. For materials for which $v_1$ is not known from other measurements, it is often possible to make an estimate of $v_1$ using the picosecond ultrasonics technique. For example, measurement of the reflection coefficient of the strain pulse at the interface between the film and the substrate, can be used to estimate the sound velocity. The reflection coefficient $r_{12}$ of sound at an interface between a film 1 and a substrate 2 is given by the formula:

$$r_{12} = \frac{Z_1 - Z_2}{Z_1 + Z_2} \quad (1)$$

where $Z_1 = \rho_1 v_1$ and $Z_2 = \rho_2 v_2$, where $\rho_1$ and $\rho_2$ being the mass density of the film and substrate, and $v_1$ and $v_2$ their sound velocities. Thus, assuming that the densities and the sound velocity in the substrate, $v_2$, are known, a measurement of $r_{12}$ can be used to determine the sound velocity, $v_1$, in the film.

Alternatively, measurement of the ultrasonic round trip time in one sample can be measured and the thickness of the sample can then be measured by scanning electron microscopy. This destroys that particular sample but provides a value of the sound velocity which can then be used to determine the thickness of other samples that have been prepared from the same material.

In addition to the determination of film thickness, the picosecond ultrasonic method can be used to determine other properties of thin film materials. These include, but are not limited to, the determination of grain size, grain orientation, adhesion between a film and a substrate, phase changes in the film material, electrical and thermal conductivity and electromigration.

With respect to grain size and orientation, the grain size of the sample results in an attenuation of the propagating sound pulses. The attenuation has a variation with frequency which results in a change in the shape of the sound pulse as it propagates. Thus, the shape of successive echoes of sound bouncing back and forth inside a thin film will be different and this change in shape gives information about the grain size of the film material. Further, in a typical picosecond ultrasonic measurement the detected change in optical reflectivity arises from (A) the propagating strain pulses, together with additional contributions from (B) the transient temperature change of the film in which the light is absorbed and (C) the sudden change in the distribution of the electrons that occurs immediately after the pump light pulse has been absorbed. These three components can be distinguished because each has a different and characteristic variation with time. From a comparison of the relative magnitudes of these three contributions it is possible to deduce the grain orientation of the sample.

With respect to the measurement of adhesion, when a film is well bonded to a substrate or to an adjacent film, the reflection of sound at the interface is given by the acoustic mismatch formula already given as Eq. (1). This reflection coefficient is independent of frequency. For a film that is poorly bonded the reflection coefficient will normally be higher and will vary with frequency. Usually, the reflection coefficient is higher at higher frequency. A variation of the reflection coefficient with frequency results in a change in the shape of the reflected sound pulse and this change in shape can be analyzed to give information about the adhesion.

Changes in the phase of the material making up a film can be detected in several ways. There will normally be a change in the sound velocity. The shape and size of the ultrasonic echoes will change. In addition, there will normally be changes in the components of the measured change in reflectivity arising from the transient temperature change and the change in the electron distribution (see (B) and (C) mentioned under grain orientation).

With respect to electrical and thermal conductivity, when the pump pulse is absorbed in the sample, energy is first given to the electrons close to the surface. These electrons diffuse rapidly into the interior of the material before they lose energy and transfer their energy to the phonons (thermal lattice vibrations). The distance over which this diffusion takes place affects the shape of the sound pulse that is generated. From a measurement of the shape of the sound pulse it is possible to make an estimate of the rate at which the electrons diffuse and from this to determine the electrical and thermal conductivity. For example, in the case of a sufficiently thin metal film of high conductivity, the electrons may diffuse throughout the thickness of the film before giving their energy to the lattice. In this case sound pulses are generated from both the front and the back of the film. The relative magnitudes of the front and back pulses is related to the conductivity.

Lastly, when a metal film carries current, electromigration can result in a change in the thickness of certain regions of the film with time. Thus, electromigration can be detected through a precision measurement of changes in the film thickness.

The above methods rely on an accurate measurement of the change in the optical reflectivity of the sample by means of an applied time-delayed probe light pulse, e.g., a measurement of the change in the intensity of the reflected probe pulse. Instead of measuring the change in the intensity of the reflected probe pulse, measurements can also be made of the change in the phase of the reflected probe pulse, the change in the polarization of the reflected probe pulse, the change in the direction of the reflected probe pulse and, in the case of samples that are partially transparent measurement of the change in the intensity of the transmitted probe pulse.

In sum, in the conventional picosecond ultrasonic technique the probe light is directed at the surface of the sample and the intensity, or other attribute (see above), of the reflected probe light is measured. Exemplary patents describing such conventional picosecond ultrasonic techniques and devices include U.S. Pat. Nos. 5,748,317 (characterizing thin film and interface characteristics using optical heat generator and detector); 5,748,318 (optical stress generator and detector); 5,959,735 (improved optical stress generator and detector); 5,864,393 (stress in thin films); 5,844,684 (mechanical properties of materials); 6,038,026 (grain size in thin films); 6,025,918 (electromigration); 6,317,216 (grain orientation); and 6,321,601 (characterizing laterally-patterned samples in an integrated circuit (IC)).

SUMMARY OF THE INVENTION

An exemplary embodiment in accordance with this invention is an improvement in the above-described conventional picosecond ultrasonic techniques and devices. The improvement features an optical cavity that causes the probe light beam to be reflected multiple times from the sample surface. As a consequence, the total change in the intensity (or other attribute) of the reflected probe beam is substantially enhanced compared to the change in reflectivity that would occur if the probe light were reflected only once, as in a conventional device.

Accordingly, another exemplary embodiment in accordance with this invention comprises an improved optical generation and detection system for non-destructively measuring the properties of a sample surface wherein the improvement comprises a reflector disposed between the probe light and above and in parallel relation to the upper surface of the sample and formed to permit the probe light to be directed through the reflector onto the surface of the sample and to be reflected multiple times from the sample surface. This disposition of the reflector above the sample surface creates an optical cavity.

A further exemplary embodiment in accordance with this invention is a method for characterizing a sample. The method includes applying a first pulse of electromagnetic radiation to the surface of the sample and thus creating a propagating strain pulse within the sample. A second pulse of second electromagnetic radiation is applied to the surface of the sample so as to intercept the propagating strain pulse. The method includes detecting at least one optical property of a reflection of the second pulse from the sample. The detected optical property(ies) of the reflection are associated with a characteristic of the sample. The first and second pulses are applied through a structure that is disposed over the surface of the sample at a distance predetermined to form an optical cavity; the cavity having a width related to a wavelength of the second electromagnetic radiation.

Another exemplary embodiment in accordance with this invention is an apparatus for characterizing a sample. The apparatus includes a first subsystem to apply a first pulse of electromagnetic radiation to a surface of the sample, thus creating a propagating strain pulse within the sample. A second subsystem can apply a second pulse of second electromagnetic radiation to the surface of the sample to intercept the propagating strain pulse. The apparatus includes a structure that is disposed over the surface of the sample at a distance predetermined to form an optical cavity having a width related to a wavelength of the second electromagnetic radiation. The first and second pulses are applied through this structure. A detection subsystem detects at least one optical property of a reflection of the second pulse from the sample. The apparatus also includes an associating subsystem to associate the detected optical property(ies) of the reflection with a characteristic of the sample.

A further exemplary embodiment in accordance with this invention is a computer-readable medium embodied with a program of computer-readable instructions. The instructions are executable by a processing unit to perform operations. The operations include applying a first pulse of electromagnetic radiation to a surface of the sample, thus creating a propagating strain pulse within the sample. There are operations to apply a second pulse of second electromagnetic radiation to the surface of the sample to intercept the propagating strain pulse. At least one optical property of a reflection of the second pulse from the sample is detected. The operations also include associating the detected optical property(ies) of the reflection with a characteristic of the sample. The first and second pulses are applied through a structure that is disposed over the surface of the sample at a distance predetermined to form an optical cavity having a width related to a wavelength of the second electromagnetic radiation.

Another exemplary embodiment in accordance with this invention is an apparatus for characterizing a sample. The apparatus includes a means for applying a first pulse of electromagnetic radiation to a surface of the sample, thus creating a propagating strain pulse within the sample. A means for applying a second pulse of second electromagnetic radiation to the surface of the sample so as to intercept the propagating strain pulse is also included. The apparatus includes a means for detecting at least one optical property of a reflection of the second pulse from the sample. A means for associating the detected optical property(ies) of the reflection with a characteristic of the sample are included. The first and second pulses are applied through a structure that is disposed over the surface of the sample at a distance predetermined to form an optical cavity having a width related to a wavelength of the second electromagnetic radiation.

A further exemplary embodiment in accordance with this invention is a reflector. The reflector includes a substrate having a first surface and a second surface opposite the first surface. At least one partially reflective film is deposited on the second surface of the substrate. The reflector is configured to be utilized to enhance a magnitude of change in a pulse of electromagnetic radiation that has interacted with a sample by reflecting the pulse so that the pulse interacts with the sample multiple times.

DETAILED DESCRIPTION

Figure 1:
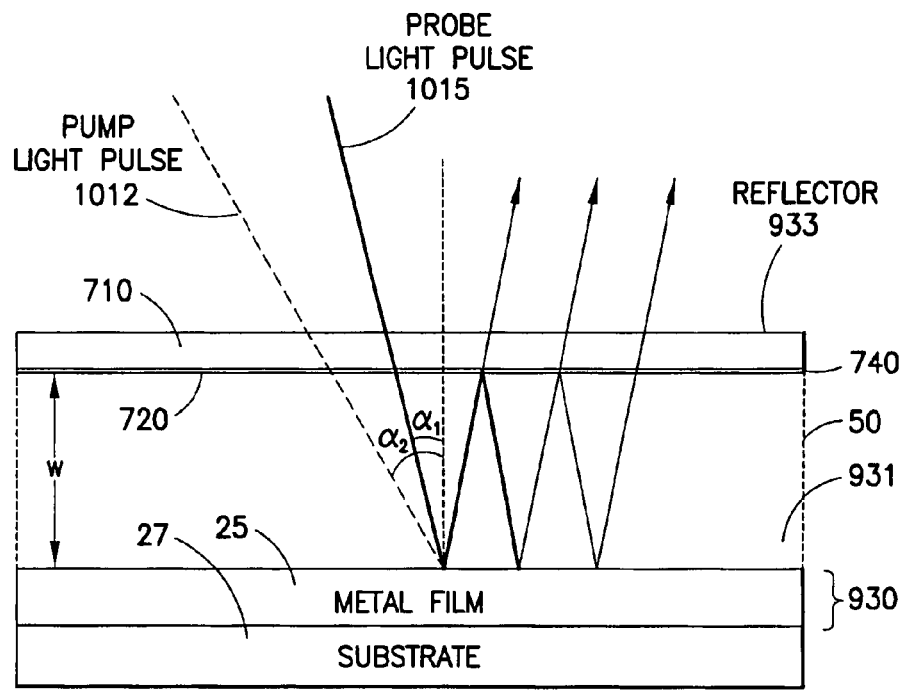
FIG. 1 is an illustration of the disposition of the reflector in an exemplary embodiment of a system in accordance with this invention.

An exemplary embodiment in accordance with this invention is shown schematically in FIG. 1. A structure (the "reflector") 933 is placed on top of the sample 930. The sample 930 consists of a metal film 25 deposited onto a substrate 27. The reflector 933 comprises a substrate 710 together with one or more than one thin films 720 deposited onto its lower surface 740. The film or films 720 may be composed of metal or of dielectric material or of combinations of the two. The spacing between the bottom of the lowest film 720 and the uppermost surface of the sample 930 is controlled and forms an optical cavity 50 between the lower surface 740 of the reflector 933 and the upper surface 931 of the sample 930.

A pump light pulse 1012 is directed through the reflector 933 onto the sample 930. This produces a sudden heating of the film surface that causes the material near to the surface of the film sample 930 to expand. As a result, a strain pulse is launched into the sample 930.

The strain pulse may propagate away from the surface 931 and into the volume of the film 25. This pulse may be partially reflected at the interface between the film 25 and the substrate 27 and may then return to the free surface 931 of the film 930. When it returns, it may cause a transient change in the optical reflectivity of the sample surface 931 and may also cause a transient displacement of the sample surface 931. This displacement of the surface may alter the spacing between the surface and the lower surface of the bottom most film 720 of the reflector 933. The reflector 933 may be mounted above the sample surface 931 so that the returning strain pulse does not materially change the position of the reflector 933.

To detect the returning sound, a probe light pulse 1015 is directed through the reflector 933 towards the sample 930. The intensity, R, of the reflected probe light 1015 is measured as a function of the time delay, t, between the pump light pulse 1012 and the probe light pulse 1015. When the time of application of the probe light pulse 1015 coincides with the time at which the strain pulse returns to the surface of the sample 930, a change in the intensity, ΔR, of the reflected probe light 1015 will be detected.

The function of the optical cavity 50 is to enhance the magnitude of this change in the intensity of the reflected probe pulse 1015, more specifically, to enhance the value of ΔR/R. By choosing the optical reflectivity of the reflector 933 and its spacing w from the uppermost surface of the sample 930 in an appropriate way, it is possible to substantially increase the value of ΔR/R compared to the value that it would have if no reflector 933 were present. This enhancement occurs when the optical cavity 50 is in a condition that is close to resonance. In this condition, some of the probe light 1015 passes through the reflector 933 and then becomes trapped in the space between the reflector 933 and the surface of the sample 930. The probe light 1015 bounces back and forth within this space being reflected multiple times at the surface of the metal film 25 on the surface of the sample 930. At each reflection at the metal film 25 a fraction of the energy is lost and light also escapes through the reflector 933.

Figure 2:
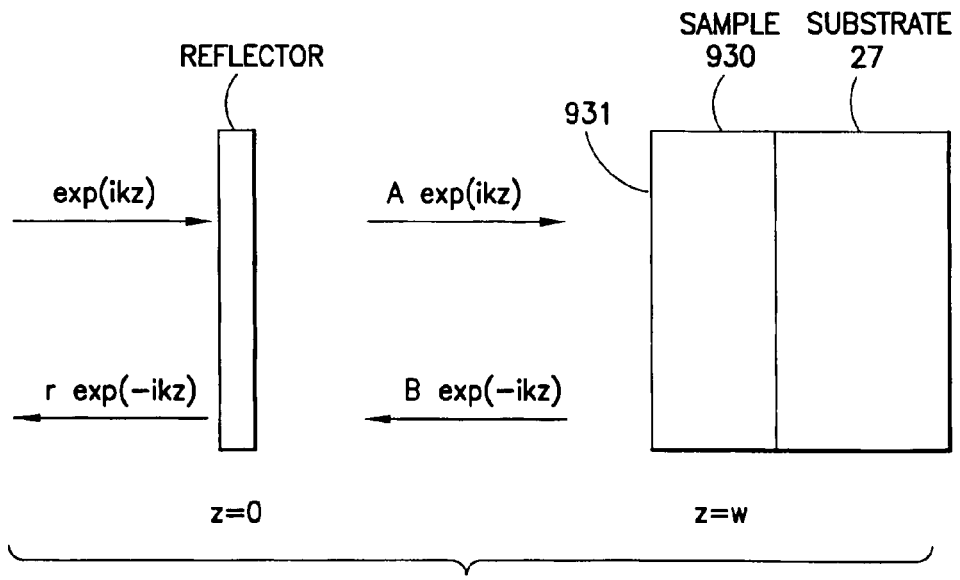
FIG. 2 is an illustration demonstrating equations (2)-(4) of the detailed description.

Referring to FIG. 2, the reflector 933 is located at the position z=0 and the sample surface 931 is at z=w The reflection coefficients at the reflector 933 from the left hand and right hand sides are $r_L$ and $r_R$, respectively. The corresponding transmission coefficients from the left and from the right are $t_L$ and $t_R$. The reflection coefficient of the sample 930 is $r_S$. The reflection coefficient from the overall structure (reflector 933 plus sample 930) is r, given by:

$$r = r_L + \frac{t_L r_S t_R \exp(2ikw)}{1 - r_R r_S \exp(2ikw)} \quad (2)$$

$$A = \frac{t_L}{1 - r_R r_S \exp(2ikw)} \quad (3)$$

$$B = \frac{t_L r_S \exp(2ikw)}{1 - r_R r_S \exp(2ikw)} \quad (4)$$

where $k=2\pi/\lambda$ and $\lambda$ is the light wavelength in free space. The intensity reflection coefficient is $R=|r|^2$.

The above equations hold when the probe light 1015 is at normal incidence; similar, yet more complicated, formulas hold if the light is at oblique incidence.

By way of an illustration of the operation of an exemplary embodiment in accordance with this invention, consider its application to measurements on a copper film. The optical reflectivity of copper has been studied by a number of researchers and slightly different results have been obtained according to the surface preparation technique and measurement method. The measurements, such as those of S. Roberts, Phys. Rev. 118, 1509 (1960), indicate that at a wavelength of 800 nm the intensity reflection coefficient for a highly-polished copper surface in vacuum is in excess of 0.98, implying that the magnitude of $r_S$ is 0.99 or larger.

Figure 3:
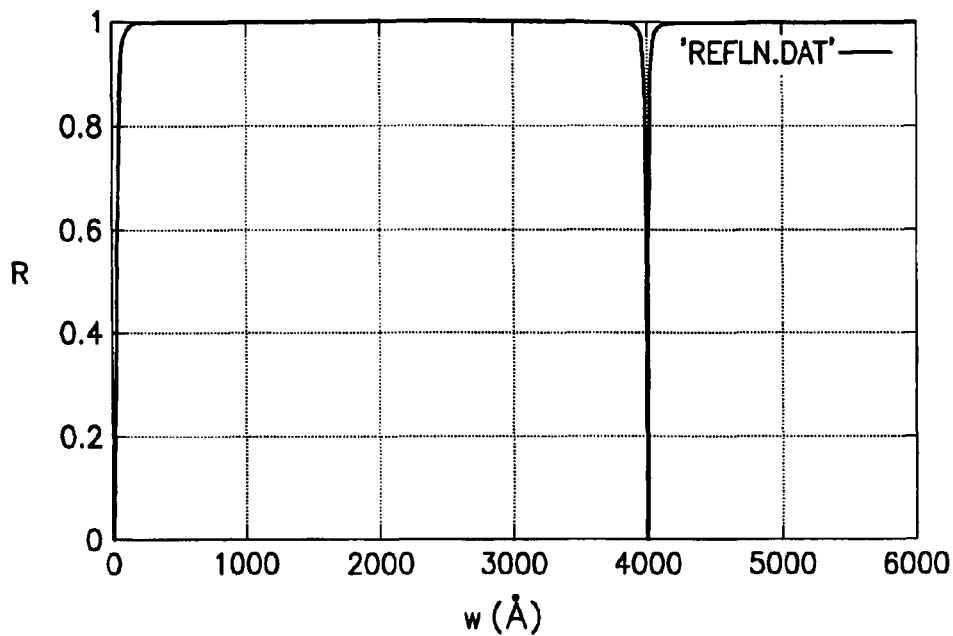
FIG. 3 is a graphic illustration showing the variation in the intensity reflection coefficient of the sample plus reflector when the amplitude reflection coefficient of the reflector has a value of −0.99.

Using an amplitude reflection coefficient $r_L=r_R$ of the reflector 933 to have the value −0.99; then the intensity reflection coefficient of the structure (reflector 933 plus sample 930) varies with the spacing w between the reflector 933 and the surface of the copper film as shown in FIG. 3. It can be seen that when w lies in the range around 4000 Å, the reflectivity is extremely sensitive to small changes in w. When a strain pulse is generated in the copper film and, after reflection at the interface to the substrate, returns to the surface of the copper film the surface of the sample 930 is displaced. This surface displacement may cause a readily measurable change in the optical reflectivity that can be measured by the time-delayed probe light pulse 1015.

Figure 4:
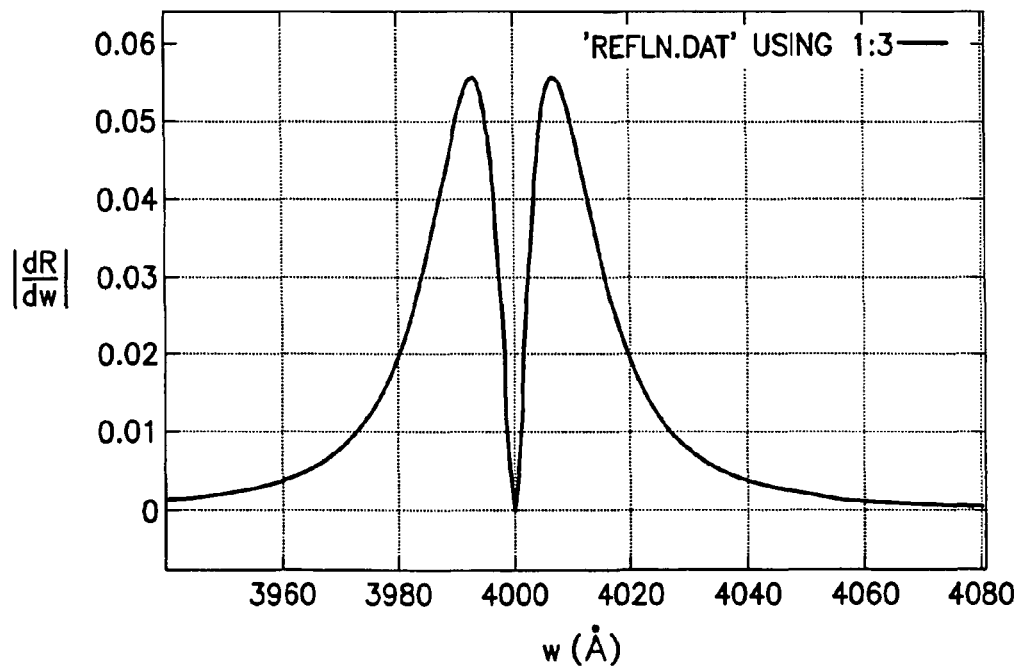
FIG. 4 is a graphic illustration of the absolute magnitude of dR/dw for the value in FIG. 3.

While the choice of a reflector 933 with a reflection coefficient of −0.99 results in a very large change of the overall reflectivity when the surface of the sample 930 moves, it may be difficult to use a system like this for all samples that are of interest. The large enhancement occurs if the spacing w lies in a very narrow range around 4000 Å. This is shown in FIG. 4 which is a plot of the absolute magnitude of dR/dw.

In the range around 4000 Å, the cavity 50 spacing is approximately one half of the wavelength of light and the cavity 50 is in resonance (however, resonance will also occur whenever the cavity spacing is an integer number of half wavelengths: $n\lambda/2$). When the reflectivity of the reflector 933 has a magnitude close to unity, the quality factor, Q, of the optical cavity 50 is large and thus the resonance is very sharp. To take advantage of this sharp resonance, it is preferable for the spacing between the reflector 933 and the sample 930 to vary by a very small amount (less than a few Å) across the area of the sample surface 931 that is illuminated with the pump 1012 and probe beams 1015. It is difficult to focus the pump 1012 and probe beams 1015 onto spots that have lateral dimensions that are less than about 1 micron. Thus, over an area with dimensions of at least 1 micron the sample 930 should be flat to a few Å. The sample surface 931 is preferably accurately parallel to the reflector 933.

For this reason, it may often be advantageous to use a reflector 933 that has an amplitude reflection coefficient with a smaller magnitude. In addition, the reflectivity of copper films that have been exposed to the atmosphere for some time may have a somewhat lower reflectivity than the samples studied by Roberts.

Figure 5:
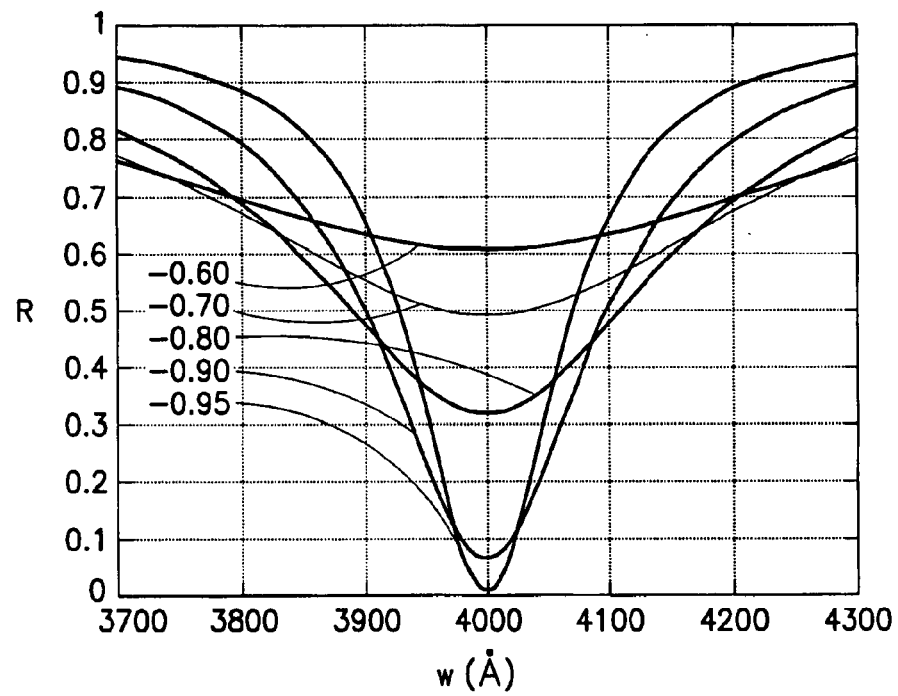
FIG. 5 is a graphic illustration showing how the intensity reflection coefficient of the sample plus reflector varies with w when the amplitude reflection coefficient of the reflector varies from −0.6 to −0.95.

FIG. 5 shows how the intensity reflection coefficient of the structure (reflector 933 plus sample 930) varies with w for a series of different values of the parameter $r_L = r_R$. The values chosen were −0.6, −0.7, −0.8, −0.9 and −0.95 and the amplitude reflection coefficient for the copper is taken to be −0.94.

Figure 6:
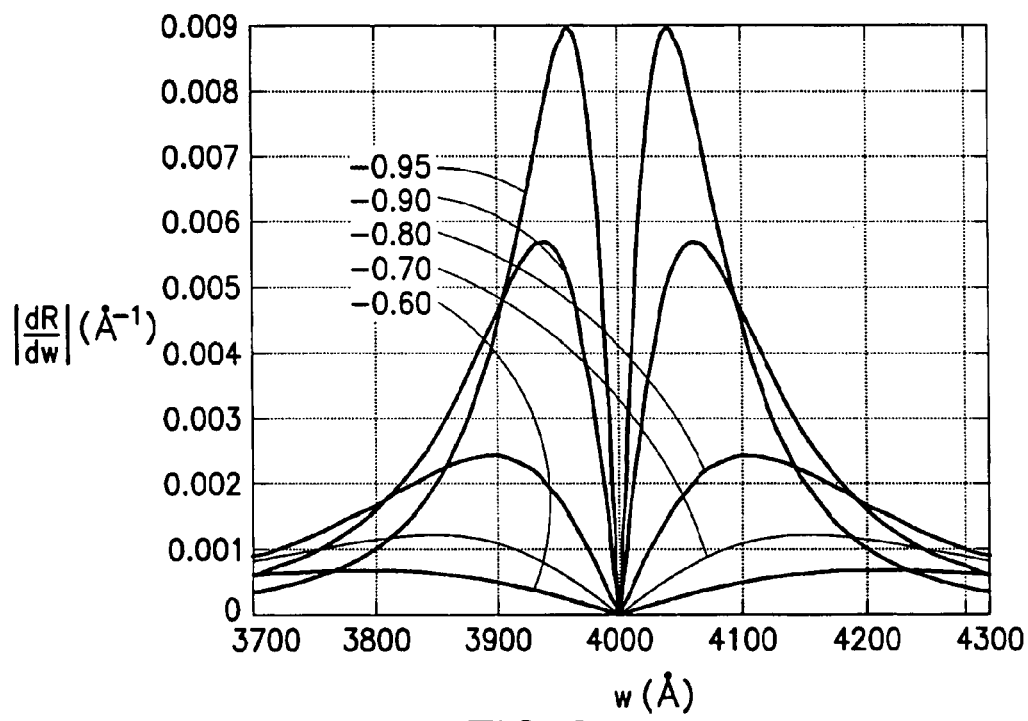
FIG. 6 is a graphic illustration of the magnitude of dR/dw for the values in FIG. 5.
Figure 7:
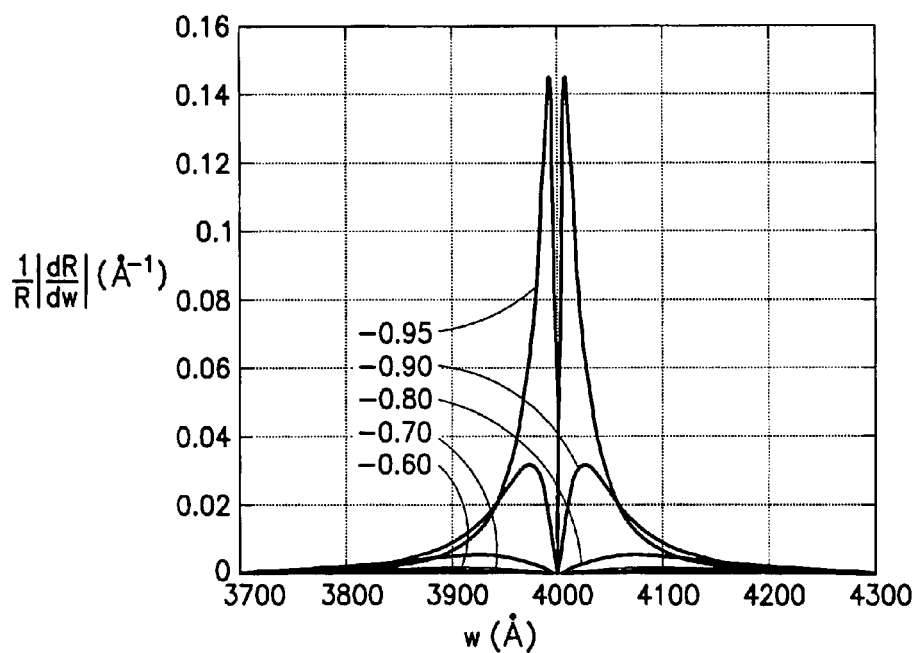
FIG. 7 is a graphic illustration of the fractional change in the intensity of the reflected probe light that results from unit displacement of the sample surface.

FIG. 6 shows the magnitude of dR/dw and FIG. 7 shows $$\frac{1}{R}\left|\frac{dR}{dw}\right|.$$

This quantity represents the fractional change in the intensity of the reflected probe light 1015 that results from unit displacement of the sample surface 931.

It can be seen from these figures that as the magnitude of the amplitude reflection coefficient at the reflector 933 decreases the maximum value of $$\frac{1}{R}\left|\frac{dR}{dw}\right|$$

is reduced. However, the range of w over which there is an appreciable value of $$\frac{1}{R}\left|\frac{dR}{dw}\right|$$

increases.

Thus, for sample surfaces that are rough it may be advantageous to use a reflector 933 with an amplitude reflection coefficient of smaller magnitude than would be advantageous for a smoother sample 930. It is recognized that the reflection coefficient of the metal film 25 may be complex rather than real. However, inclusion of the phase shift on reflection does not change the maximum value of $$\frac{1}{R}\left|\frac{dR}{dw}\right|,$$

but simply causes a shift of the plots of R, dR/dw and $$\frac{1}{R}\left|\frac{dR}{dw}\right|$$

versus w along the horizontal axis.

The calculations presented concern the change in R when there is a small displacement of the surface. The returning strain pulse may also cause a change in the optical constants of the surface of the metal film 25 and this may result in a change in R. This change can readily be calculated from Eq. (2). The change dR in the reflected intensity of the probe pulse may be largest when the width w of the optical cavity 50 is such that the cavity 50 is close to resonance condition. The change dR may arise from both the change in the magnitude and the change in the phase of the amplitude reflection coefficient at the sample surface 931.

By means of a suitable choice of the spacing w between the reflector 933 and the surface of the sample 930, it is possible to make the measured change dR in the reflected intensity of the probe pulse 1015 be primarily a measure of the change in w due to the displacement of the sample surface 931 or to be primarily a measure of the change in the reflection coefficient at the sample surface 931.

The above description has considered a system in which the measured quantity is the change in the intensity of the reflected probe light 1015. It is also within the scope of this invention to measure the change in the phase of the reflected probe pulse 1015, the change in the polarization of the reflected probe pulse 1015, the change in the direction of the reflected probe pulse 1015 and, in the case of samples that are partially transparent measurement of the change in the intensity of the transmitted probe pulse 1015.

It is within the scope of the invention to use different wavelengths for the pump 1012 and probe beams 1015. It is advantageous for the wavelength of the probe light 1015 to be such that the reflectivity of the sample 930 is high. In this situation, it is possible to make an optical cavity 50 with a high quality factor in which the probe light 1015 may be reflected many times from the sample 930. The wavelength of the pump light can be selected so that its transmission through the reflector 933 is high. It may, in some circumstances, be advantageous to apply the pump 1012 and probe beams 1015 to the sample 930 with different angles of incidence, $\alpha_1$ and $\alpha_2$. For example, the angle of the probe $\alpha_1$ can be chosen so that the reflectivity of the reflector 933 is high (this is needed to make an effective optical cavity 50), but the pump 1012 can be directed at a different angle, $\alpha_2$, such that the most of the pump light 1012 is transmitted through the reflector 933 to reach the sample 930.

The wavelengths of the pump 1012 and probe light 1015 can lie in the range between 100 microns and 0.1 micron. The energy in each pump 1012 and probe light pulse 1015 can lie in the range between $10^{-14}$ J and $10^{-3}$ J. The duration of each pump 1012 and probe light 1015 can lie in the range from $10^{-14}$ s to $10^{-6}$ s.

The pump 1012 and probe light pulses 1015 can be provided from a single laser or from two separate lasers. In the event that the pump 1012 and probe 1015 come from the same laser their timing may be synchronized. The time delay between each pump pulse used to generate a strain pulse and the probe pulse used to detect the strain pulse can be controlled by means of an adjustable optical path. The time delay can be changed through the provision in the optical path of a variable position stage.

If two lasers are used, they can be synchronized in which case the time delay can be controlled by the same method as is used when both pulses come from a single laser. If the two lasers are not synchronized, a different system can be used that is referred to as asynchronous detection (AD). With this method, the pump laser has a repetition frequency that is slightly larger than the repetition frequency of the probe laser. For example, the frequency of the pump laser could be 100.01 MHz and the probe laser 100 MHz. Then, as time elapses, the time delay between a pump pulse 1012 and the next probe pulse 1015 increases at a small and steady rate, reaches a maximum value that is approximately equal to the time of 10 nsecs between successive probe light pulses 1015 and then goes back to a small value and begins to increase again. Measurements are made by recording the intensity (or other attribute) of the reflected probe light 1015 with a transient recorder. For details of this measurement method, see A. Bartels et al., "Femtosecond time-resolved optical pump-probe spectroscopy at kHz-scan-rates over ns-time-delays without mechanical delay line", Appl. Phys. Lett. 88, 041117 (2006).

The pump 1012 and probe light 1015 beams can be brought to the reflector 933 plus sample 930 using standard optical components to guide the beams such as mirrors, lenses, prisms, etc. The positioning of the pump 1012 and probe beams 1015 can be controlled through the use of an auto-focus system. It is also within the scope of the invention to bring the light to the sample 930 using one or more optical fibers. Optical fibers can be used to maintain the focusing of the beams on the sample 930, such as described by W. S. Capinski and H. J. Maris, "Improved apparatus for picosecond pump-and-probe optical measurements", Review of Scientific Instruments, 67, 2720 (1998).

While the examples that have been listed here of the utility exemplary embodiments in accordance with this invention have concerned the measurement of the properties of metallic films such as copper and aluminum, the invention is not restricted to the study of these materials. It is preferable that the sample 930 have a high optical reflectivity. For example, the sample 930 could consist of any one the following:

1) A substrate 27, followed by a series of metal films 25 of different thickness. The strain pulse would be generated at the free surface of the uppermost metal film. The strain pulse would propagate into the sample 930 and be partially reflected at each interface. This would result in a series of echoes returning to the upper surface of the sample 930.
2) A substrate 27, followed by a series of metal films 25 of different thickness and then a transparent film. The strain pulse would again be generated at the free surface of the uppermost metal film. The absorption of the pump light pulse 1012 would cause a stress to be set up in the uppermost metal film. This stress would cause one strain pulse to be generated that would propagate down through the lower metal layers and a second strain pulse that propagates into the transparent film. These two strain pulses may be partially reflected at each interface that is encountered. An analysis of the change in reflectivity $\Delta R$ of the structure provides information about the thickness and other characteristics of each film in the structure.
3) A substrate 27, onto which have been deposited a metal film, or films, 25 that have been laterally patterned. This includes, for example, a metal film that has been patterned to form a series of lines running across the sample 930. Such structures can have a high optical reflectivity and hence the signal $\Delta R$ that is detected can be substantially enhanced through the use of an optical cavity 50.

It is important to appreciate the distinction between the present invention and methods in which some type of interferometer is used to measure the displacement of a sample surface 931 after a strain pulse has been generated in the sample 930. There are several different types of interferometer that can be used, e.g. Michelson, Sagnac, etc. When these interferometers are used, the probe light 1015 that is reflected from the surface of the sample interferes with a reference beam.

The reference beam can be selected in different ways. It can be a beam that has not been reflected from the sample 930, it can be a beam that has been reflected from the sample 930 at a location other than the location in which the strain pulse is propagating, or it can be a beam that has been reflected from the sample 930 at a time such that the strain pulse is not impinging on the sample surface 931. However, in all cases the interference is between a probe beam 1015 that has been reflected from the surface of the sample 930 at the time of arrival of a strain pulse and a second beam for which the amplitude and phase have not been influenced by the presence of a strain pulse.

In contrast, in the present invention the optical cavity 50 makes it possible for the probe beam to be reflected multiple times from the surface of the sample 930, thereby causing a large total change in the characteristics of the reflected probe beam 1015. In this regard, it is noted that if the light wavelength is 8000 Å and the optical cavity 50 spacing w is 4000 Å, the time between the successive reflections of the probe light 1015 at the surface of the sample 930 is 2.7 fs. Thus all of these reflections of the probe light 1015 occur within a very short time range (e.g., 30 fs) in which the change in position of the surface of the sample 930 due to the returning strain pulse is very small.

Figure 8:
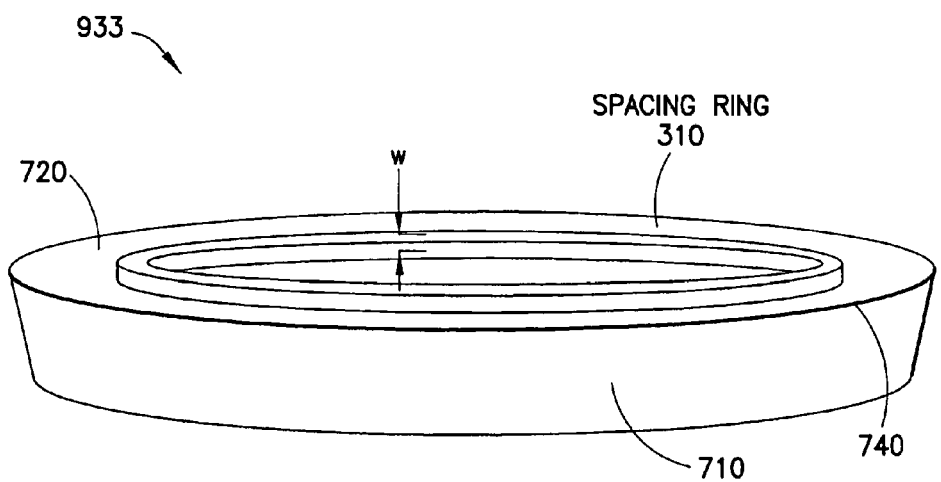
FIG. 8 is a block diagram of a reflector with a spacing ring.
Figure 9:
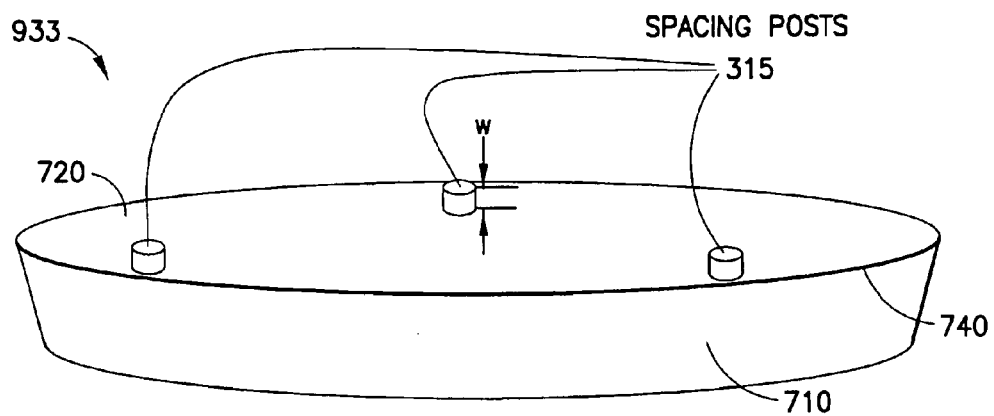
FIG. 9 is a block diagram of a reflector with spacing posts.

The alignment and the spacing of the reflector 933 may be well controlled to be accurately parallel to the surface of the sample 930. Consequently, the reflector 933 may include means for aligning and maintaining in parallel the lower surface of the reflector 933 and the upper surface of the sample 930. There is a wide range of possible designs for the reflector 933 to accomplish this. For example, the reflector 933 could have a raised ring 310 on the surface that is adjacent to the sample 930, e.g., the lower surface and the thickness of the ring 310 would set the spacing w as illustrated in FIG. 8. The pump and probe beams are directed to the area within the ring 310. Alternatively, there could be a number of posts 315 and the pump 1012 and probe beams 1015 directed to the area between the posts as illustrated in FIG. 9.

It is important to note that since the strain pulses are generated in the region inside the means for maintaining the parallel spacing of the surfaces (for example, the ring 310 or the area occupied by the posts 315), the excitation and propagation of the strain pulses may not result in a motion of the reflector 933.

Figure 10:
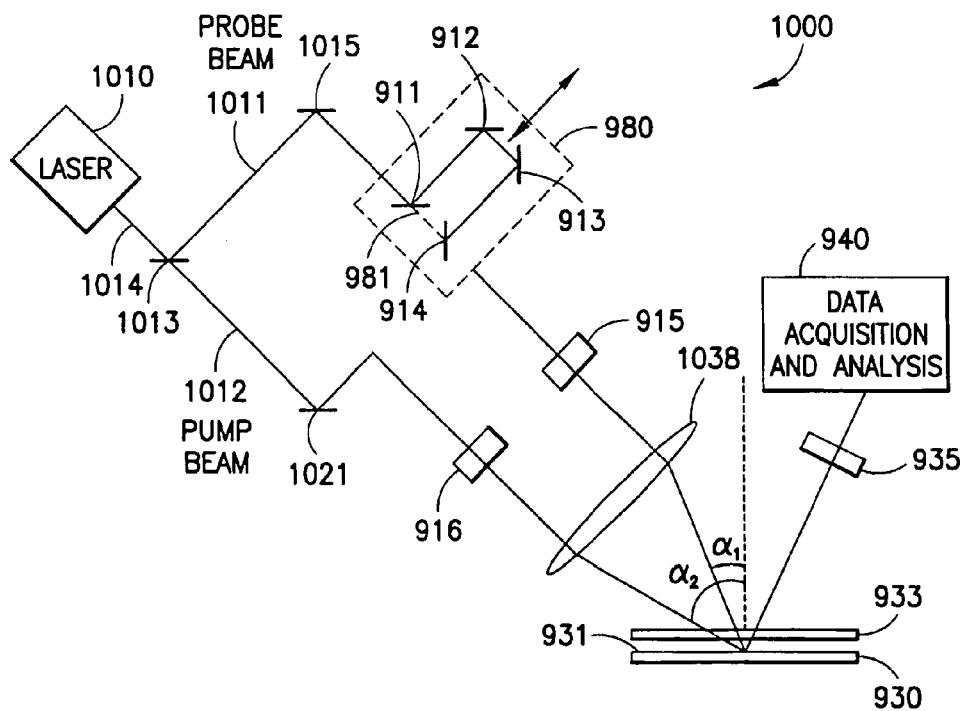
FIG. 10 is a block diagram of an exemplary system for performing detection with separate pump and probe beams.

Referring to FIG. 10, an exemplary system 1000 is shown for performing detection with separate pump and probe beams. System 1000 includes a laser 1010 and mirrors 911, 912, 913 and 914. System 1000 includes a splitter 1013 that creates both pump beam 1012 and probe beam 1011 from one light beam 1014 from laser 1010. The mirrors 912 and 913 are movable to produce a time delay between the pump beam 1012 and probe beam 1011. The mirrors 911-914 form a time delay mechanism 980. The mirrors 911-914 are merely one example of a time delay mechanism 980 and any mechanism for adjusting delay between the probe beam 1011 and the pump beam 1012 may be used. In this example, delay is adjusted by positioning of the time delay mechanism 980.

The system 1000 also includes polarizers $P_2$ 915, $P_1$ 916, an analyzer 935 and a data acquisition and analysis module 940 (which includes in this example a detector that is not shown). The pump beam 1012 and probe beam 1011 are directed through the reflector 933 onto the surface 931 of the sample 930 at particular angles of incidence, $\alpha_1$ and $\alpha_2$.

Note that in this example, the probe beam 1011 may also bypass the time delay mechanism 980 by following path 981. Path 981 may be created by removing mirrors 911, 914 or by moving the mirrors 911, 914 so that the mirrors do not impede the probe beam 1011. A lens 1038 is used to focus the pump beam 1012 and probe beam 1011 onto the surface 931 of the sample 930. It should be appreciated that system 1000 is an exemplary and non-limiting example of a system that may be used in accordance with this invention.

Figure 11:
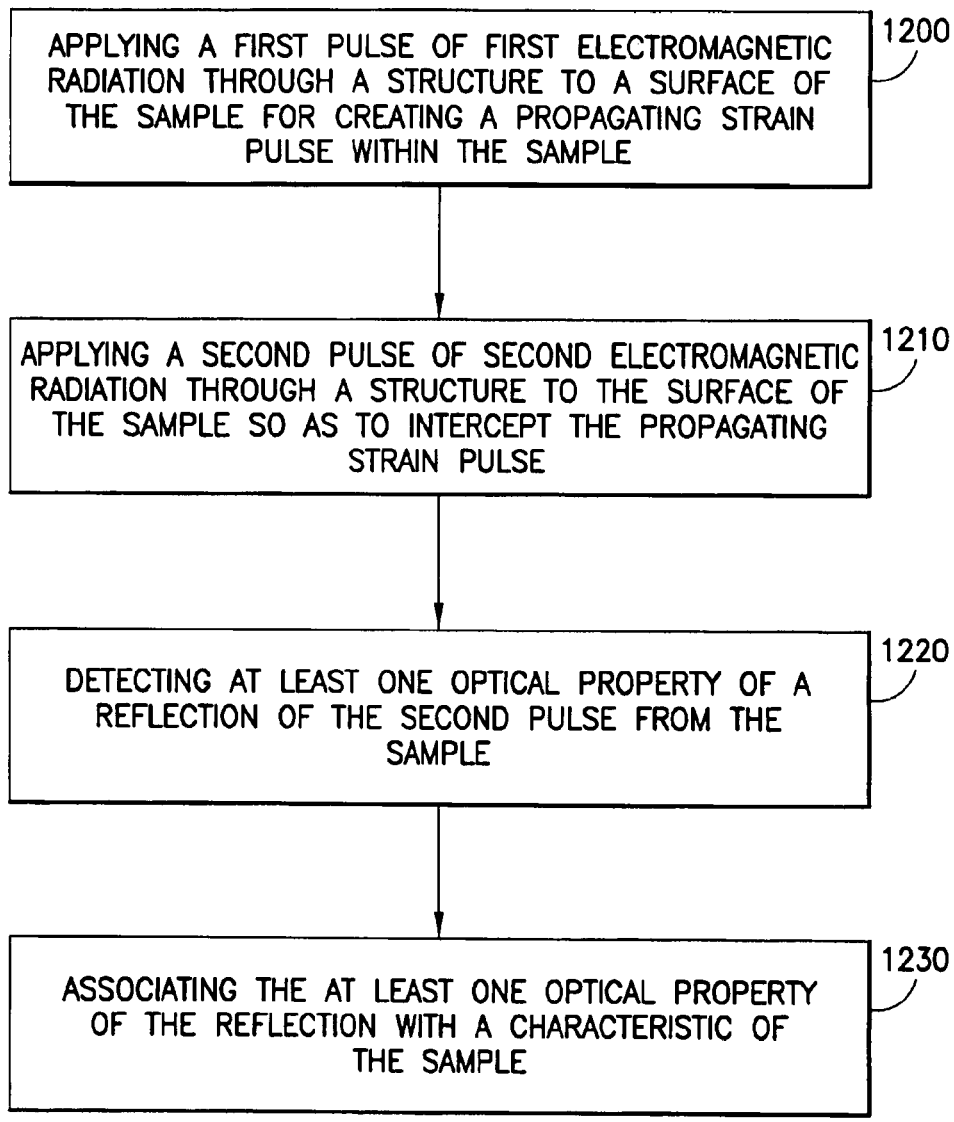
FIG. 11 is a logic flow diagram of an exemplary embodiment in accordance with this invention of a method for characterizing a sample.

FIG. 11 is a logic flow diagram of an exemplary embodiment in accordance with this invention of a method for characterizing a sample 930. At block 1200, a first pulse of electromagnetic radiation is applied to the surface of the sample creating a propagating strain pulse within the sample. A second pulse of second electromagnetic radiation is applied to the surface of the sample so as to intercept the propagating strain pulse, in block 1210. The first and second pulses are applied through a structure that is disposed over the surface of the sample at a distance predetermined to form an optical cavity; the cavity having a width related to a wavelength of the second electromagnetic radiation. At block 1220, at least one optical property of a reflection of the second pulse from the sample is detected. The detected optical property(ies) of the reflection are associated with a characteristic of the sample in block 1230.

A further exemplary embodiment in accordance with this invention is a method for characterizing a sample. The method includes applying a first pulse of electromagnetic radiation to the surface of the sample and thus creating a propagating strain pulse within the sample. A second pulse of second electromagnetic radiation is applied to the surface of the sample so as to intercept the propagating strain pulse. The method includes detecting at least one optical property of a reflection of the second pulse from the sample. The detected optical property(ies) of the reflection are associated with a characteristic of the sample. The first and second pulses are applied through a structure that is disposed over the surface of the sample at a distance predetermined to form an optical cavity; the cavity having a width related to a wavelength of the second electromagnetic radiation.

In a further embodiment of the method as above, the detected optical property(ies) of the second pulse are detected after multiple reflections between the surface of the sample and the structure.

In other embodiments of any of the methods as above, the structure is disposed to be relatively parallel to the surface of the sample.

In further embodiments of any of the methods as above, the structure is disposed at a distance so that the second pulse will be at resonance within the optical cavity. The distance may be approximately an integer number of half wavelengths of the probe light beam from the sample.

In other embodiments of any of the methods as above, the sample is relatively flat in areas where the first and second pulses are applied.

In further embodiments of any of the methods as above, the method also includes selecting angles of incidence for the first and second pulses. The angles of incidence are selected based upon a reflectivity of the structure. Additionally, the angle of incidence for the first pulse may be selected to reduce effects of transmission through the structure on the first pulse. The angle of incidence for the second pulse may be selected to so that a reflectivity of the structure in relation to the second pulse is high.

In other embodiments of any of the methods as above, the method also includes selecting a wavelength for the first pulse to reduce effects of transmission through the structure.

In further embodiments of any of the methods as above, the detected optical property(ies) may be any of intensity, phase, polarization and direction.

In other embodiments of any of the methods as above, the associated characteristic of the sample is the thickness of the sample.

Another exemplary embodiment in accordance with this invention is an apparatus for characterizing a sample. The apparatus includes a first subsystem to apply a first pulse of electromagnetic radiation to a surface of the sample, thus creating a propagating strain pulse within the sample. A second subsystem can apply a second pulse of second electromagnetic radiation to the surface of the sample to intercept the propagating strain pulse. The apparatus includes a structure that is disposed over the surface of the sample at a distance predetermined to form an optical cavity having a width related to a wavelength of the second electromagnetic radiation. The first and second pulses are applied through this structure. A detection subsystem detects at least one optical property of a reflection of the second pulse from the sample. The apparatus also includes an associating subsystem to associate the detected optical property(ies) of the reflection with a characteristic of the sample.

In a further embodiment of the apparatus as above, the detected optical property(ies) of the second pulse are detected after multiple reflections between the surface of the sample and the structure.

In a further embodiment of any of the apparatuses as above, the structure includes a spacer for aligning a lower surface of the structure and the surface of the sample. The spacer may be a ring or a set of posts. The spacer may also be configured to align the structure at a distance so that the second pulse will be at resonance within the optical cavity.

Another exemplary embodiment in accordance with this invention is a computer-readable medium embodied with a program of computer-readable instructions. The instructions are executable by a processing unit to perform operations. The operations include applying a first pulse of electromagnetic radiation to a surface of the sample, thus creating a propagating strain pulse within the sample. There are operations to apply a second pulse of second electromagnetic radiation to the surface of the sample to intercept the propagating strain pulse. At least one optical property of a reflection of the second pulse from the sample is detected. The operations also include associating the detected optical property(ies) of the reflection with a characteristic of the sample. The first and second pulses are applied through a structure that is disposed over the surface of the sample at a distance predetermined to form an optical cavity having a width related to a wavelength of the second electromagnetic radiation.

In a further embodiment of the computer-readable medium as above, the detected optical property(ies) of the second pulse are detected after multiple reflections between the surface of the sample and the structure.

In a further embodiment of any of the apparatuses as above, the operations also include selecting angles of incidence for the first and second pulses. The angles of incidence are selected based upon a reflectivity of the structure.

In a further embodiment of any of the apparatuses as above, the operations also include selecting a wavelength for the first pulse to reduce effects of transmission through the structure.

A further exemplary embodiment in accordance with this invention is a structure for reflecting a pulse of electromagnetic radiation. The structure includes a substrate having two surfaces opposite each other. At least one partially reflective film is deposited on one surface of the substrate. The structure is configured to be utilized to enhance a magnitude of change in a pulse of electromagnetic radiation that has interacted with a sample by reflecting the pulse so that the pulse interacts with the sample multiple times.

In a further embodiment of the structure as above, the substrate can allow a first pulse of first electromagnetic radiation suitable for creating a propagating strain pulse within a sample through the substrate and allow a second pulse of second electromagnetic radiation suitable to intercept the propagating strain pulse through the substrate.

In a further embodiment of any of the structures as above, the films reflect at least a portion of the second pulse when the pulse is directed at the second surface.

In a further embodiment of any of the structures as above, the structure also includes a spacer on the reflective surface of the substrate. The spacer may be a ring or a set of posts. The spacer may also align the reflective surface of the substrate to be relatively parallel with an upper surface of the sample when the structure is placed on top of the sample.

In a further embodiment of the structure as above, the spacer maintains the reflective surface of the substrate at a predetermined distance from an upper surface of the sample when the structure is placed on top of the sample. The distance may be based upon a wavelength of the reflected pulse. The distance may be an integer number of half wavelengths of the reflected pulse. The distance may be approximately 4000 Å.

In a further embodiment of any of the structures as above, the films are composed of one or more of metal and dielectric material.

In a further embodiment of any of the structures as above, the reflection coefficient of the structure is above −0.6. The reflection coefficient of the structure may be −0.99.

The foregoing description has provided by way of exemplary and non-limiting examples a full and informative description of the invention. However, various modifications and adaptations may become apparent to those skilled in the relevant arts in view of the foregoing description, when read in conjunction with the accompanying drawings and the appended claims. However, all such and similar modifications of the teachings of this invention will still fall within the scope of this invention.

Furthermore, some of the features of the preferred embodiments of this invention could be used to advantage without the corresponding use of other features. As such, the foregoing description should be considered as merely illustrative of the principles of the invention and not in limitation thereof.

The invention claimed is:

1. A method for characterizing a sample, comprising:
providing a structure that is disposed over a surface of the sample at a predetermined distance to form an optical cavity having a width, where the sample comprises at least one metal film deposited onto a substrate and the structure comprises at least one partially reflective film deposited on a surface of the structure;
creating a propagating strain pulse within the sample by applying a first pulse of first electromagnetic radiation through the structure to the surface of the sample;
applying a second pulse of second electromagnetic radiation through the structure to the surface of the sample so as to intercept the propagating strain pulse, wherein the width of the optical cavity is based at least in part on a wavelength of the second electromagnetic radiation;
detecting at least one optical property of a reflection of the second pulse from the sample; and
associating the at least one optical property of the reflection with a characteristic of the sample.

2. The method of claim 1, wherein the at least one optical property of the second pulse is detected after multiple reflections between the surface of the sample and the structure.

3. The method of claim 1, wherein the structure is disposed so that the at least one partially reflective film is relatively parallel to the surface of the sample.

4. The method of claim 1, wherein the structure is disposed at a distance so that the second pulse will be at resonance within the optical cavity.

5. The method of claim 4, wherein the distance is approximately an integer number of half wavelengths of the second pulse.

6. The method of claim 1, wherein the sample is relatively flat in areas where the first and second pulses are applied.

7. The method of claim 1, further comprising selecting angles of incidence for the first and second pulses; wherein the angles of incidence are selected based upon a reflectivity of the structure.

8. The method of claim 7, wherein the angle of incidence for the first pulse is selected to reduce a transmission through the structure of the first pulse.

9. The method of claim 7, wherein the angle of incidence for the second pulse is selected to enhance a reflectivity of the structure to the second pulse.

10. The method of claim 1, further comprising selecting a wavelength for the first pulse to reduce effects of transmission through the structure.

11. The method of claim 1, wherein the at least one detected optical property is at least one of intensity, phase, polarization and direction.

12. The method of claim 1, wherein the associated characteristic of the sample is the thickness of the sample.

13. An apparatus for characterizing a sample, comprising:
a structure disposed over a surface of the sample at a predetermined distance to form an optical cavity having a width, where the sample comprises at least one metal film deposited onto a substrate and the structure comprises at least one partially reflective film deposited on a surface of the structure;
a first electromagnetic radiation generator configured to create a propagating strain pulse within the sample by applying a first pulse of first electromagnetic radiation through the structure to the surface of the sample;
a second electromagnetic radiation generator configured to apply a second pulse of second electromagnetic radiation through the structure to the surface of the sample so as to intercept the propagating strain pulse, wherein the width of the optical cavity is based at least in part on a wavelength of the second electromagnetic radiation;
a detector configured to detect at least one optical property of a reflection of the second pulse from the sample; and
a computer configured to associate the at least one optical property of the reflection with a characteristic of the sample.

14. The apparatus of claim 13, wherein the at least one optical property of the second pulse is detected by the detector after the second pulse reflects multiple between the surface of the sample and the structure.

15. The apparatus of claim 13, wherein the structure further comprises a spacer configured to align the at least one partially reflective film is of the structure and the surface of the sample to be relatively parallel.

16. The apparatus of claim 15, wherein the spacer aligns the structure at a distance so that the second pulse will be at resonance within the optical cavity.

17. The apparatus of claim 13, wherein the structure comprises a spacer configured to maintain a lower surface of the structure and the surface of the sample at predetermined distance.

18. The apparatus of claim 17, wherein the spacer is one of a ring and a set of posts.

19. A non-transitory computer-readable medium embodied with a program of computer-readable instructions, the instructions executable by a processing unit to perform operations comprising:
   creating a propagating strain pulse within the sample by applying a first pulse of first electromagnetic radiation through a structure to a surface of the sample,
   where the structure is disposed over the surface of the sample at a predetermined distance to form an optical cavity having a width, where the sample comprises at least one metal film deposited onto a substrate and the structure comprises at least one partially reflective film deposited on a surface of the structure;
   applying a second pulse of second electromagnetic radiation through the structure to the surface of the sample so as to intercept the propagating strain pulse, wherein the width of the optical cavity is based at least in part on a wavelength of the second electromagnetic radiation;
   detecting at least one optical property of a reflection of the second pulse from the sample; and
   associating the at least one optical property of the reflection with a characteristic of the sample.

20. The computer-readable medium of claim 19, wherein the at least one optical property of the second pulse is detected after multiple reflections between the surface of the sample and the structure.

21. The computer-readable medium of claim 19, further comprising selecting angles of incidence for the first and second pulses; wherein the angles of incidence are selected based upon a reflectivity of the structure.

22. The computer-readable medium of claim 19, further comprising selecting a wavelength for the first pulse to reduce effects of transmission through the structure.

23. An apparatus for characterizing a sample, comprising:
   means for creating a propagating strain pulse within the sample by applying a first pulse of first electromagnetic radiation to a surface of the sample;
   means for applying a second pulse of second electromagnetic radiation to the surface of the sample so as to intercept the propagating strain pulse;
   means for establishing a resonant cavity over the surface of the sample that is disposed over the surface of the sample at a distance predetermined to form an optical cavity having a width related to a wavelength of the second electromagnetic radiation, where the sample comprises at least one metal film deposited onto a substrate and the structure comprises at least one partially reflective surface;
   means for detecting at least one optical property of a reflection of the second pulse from the sample; and
   means for associating the at least one optical property of the reflection with a characteristic of the sample.

24. The apparatus of claim 23, wherein the at least one optical property of the second pulse is detected after multiple reflections between the surface of the sample and the structure.

25. The apparatus of claim 23, wherein the first pulse applying means is a first laser, the second pulse applying means is a second laser, the resonant cavity means is a reflector, the detecting means is a detector, and the associating means is a processing unit.

* * * * *

UNITED STATES PATENT AND TRADEMARK OFFICE
CERTIFICATE OF CORRECTION

PATENT NO. : 8,537,363 B2
APPLICATION NO. : 12/312692
DATED : September 17, 2013
INVENTOR(S) : Humphrey J. Maris Page 1 of 1

It is certified that error appears in the above-identified patent and that said Letters Patent is hereby corrected as shown below:

In the Specification

Col. 1, line 13, please insert -- GOVERNMENT GRANT --

Col. 1, line 14, please insert -- This invention was made with government support under DMR0605355 awarded by National Science Foundation. The government has certain rights in the invention. --

Signed and Sealed this
Seventh Day of April, 2015

Michelle K. Lee
*Director of the United States Patent and Trademark Office*